United States Patent [19]

Stafford et al.

[11] Patent Number: 5,014,216

[45] Date of Patent: May 7, 1991

[54] CONCENTRATION DETERMINATION WITH MULTIPLE WAVELENGTH FLASH PHOTOMETERS

[75] Inventors: Roger A. Stafford, Orange; Roy W. Aday, Jr., Trona; Robert L. Schmidt, Yorba Linda; Myron L. McCollum, Anaheim, all of Calif.

[73] Assignee: Beckman Instruments, Inc., Fullerton, Calif.

[21] Appl. No.: 221,476

[22] Filed: Jul. 19, 1988

[51] Int. Cl.$^5$ .......................................... G01N 21/00
[52] U.S. Cl. ................................................... 364/496
[58] Field of Search ............... 364/496, 497, 498, 577, 364/573; 73/1 R, 23.1, 61.1 R, 61.1 C; 356/328, 336, 320

[56] References Cited

U.S. PATENT DOCUMENTS

| | | |
|---|---|---|
| 3,794,425 | 2/1974 | Smith et al. .......................... 250/345 |
| 3,810,696 | 5/1974 | Hutchins Jr. .......................... 356/93 |
| 3,820,901 | 6/1974 | Kreuzer .......................... 250/345 |
| 4,236,894 | 12/1980 | Sommervold .......................... 23/230 R |
| 4,241,998 | 12/1980 | Farkas et al. .......................... 356/319 |
| 4,263,512 | 4/1981 | Sagusa et al. .......................... 250/345 |
| 4,267,572 | 5/1981 | Witte .......................... 364/498 |
| 4,455,084 | 6/1984 | Webb, Jr. et al. .......................... 356/72 |
| 4,482,966 | 11/1984 | Mito et al. .......................... 364/497 |
| 4,526,470 | 7/1985 | Kaye .......................... 356/319 |
| 4,544,271 | 10/1985 | Yamamoto .......................... 356/328 |
| 4,565,447 | 1/1986 | Nelson .......................... 356/319 |
| 4,587,624 | 5/1986 | Banno .......................... 364/573 |
| 4,590,574 | 5/1986 | Edmonds et al. .......................... 364/498 |
| 4,631,687 | 12/1986 | Kowalski et al. .......................... 364/497 |
| 4,642,778 | 2/1987 | Hiefese et al. .......................... 364/498 |
| 4,674,880 | 6/1987 | Seki .......................... 356/328 |
| 4,687,329 | 8/1987 | Schultz .......................... 356/328 |
| 4,696,570 | 9/1987 | Joliot et al. .......................... 356/319 |
| 4,715,712 | 12/1987 | Nogami .......................... 356/328 |
| 4,807,148 | 2/1989 | Lacey .......................... 364/498 |

FOREIGN PATENT DOCUMENTS 0121404 10/1984 European Pat. Off. .
0195339 9/1986 European Pat. Off. .
56746330 11/1982 Japan .
1173332 12/1969 United Kingdom .

OTHER PUBLICATIONS

Plackett, R. L., *Principles of Regression Analysis*, pp. 33–51, Clarendon Press, Oxford, (1960).
Loosbroek et al., *Analytical Letters*, 17 (A8), 677–688 (1984), "Identification of Mixtures of Synthetic Organic Pigments Using UV-VIS Spectrophotometry and Kalman Filtering".
Zwart et al., *Clinical Chemistry*, 27:11, 1903–1907 (1981), "Determination of Hemoglobin Derivatives with the IL 282 CO-Oximeter as Compared with a Manual Spectrophotometric Five-Wavelength Method".
Margenau, H., and Murphy, G. M., *The mathematics of Physics and Chemistry*, pp. 311–332, D. Van Nostrand Company, Inc., Princeton, N.J. (1956).

*Primary Examiner*—Parshotam S. Lall
*Assistant Examiner*—Ellis B. Ramirez
*Attorney, Agent, or Firm*—William H. May; Gary T. Hampson; Charles Berman

[57] ABSTRACT

A monobeam system for determining concentration changes of chromophore substance in a sample includes a flash lamp for passing a light beam through a sample containing the analyte. The values of absorbance by the sample at multiple wavelengths are measured and the optimum linear combination of absorbance values is determined to obtain a measure of chromophore concentration. Extinction coefficients for a chromophore is measured employing Deming's method and eigenvector transformations. A matrix reflecting the noise pattern of the system is determined. This matrix and the extinction coefficients are used in determining the coefficients for the optimum linear combination. An electronic module converts analog intensity data into digital data for five wavelengths. This is processed into absorbance values and concentration determinations.

48 Claims, 6 Drawing Sheets

$k*e=1$
$kFk'=min$

CONCENTRATION DETERMINATION WITH MULTIPLE WAVELENGTH FLASH PHOTOMETERS

BACKGROUND

This invention relates to clinical chemistry analyzers, systems and methods. In particular, it relates to instruments for measuring the concentration, and changes of concentration, in a chromophore substance indicating the amount of a particular analyte present in a sample.

Different systems are known for measuring the concentration of a chromophore in samples. In one known form these instruments are based on a steady state lamp source passing a steady light beam through the sample. The steady state lamp source may use a tungsten-halogen filament. The power of such a lamp is about 50 to 100 watts and in the steady state operation from 1 to 15 minutes to upwards of 1 hour exposure to the lamp source is needed to provide an operational analytic system for the samples.

Another characteristic of some known steady state system is the use of a first light beam which passes through the sample. A second light beam is split off from the first light beam and is used as a reference beam. The two light beams are physically spatially separated. Electronic switch means exposes the detector and measuring electronics alternately, and thus not simultaneously, to measure multiple wavelengths coming from each of the beams of the steady light beam source. This is complicated, and the switching back and forth between the physically spaced beams may not provide for as precise a system as desirable.

In yet another form of known system a single set of optics is used and a reference beam followed by a sampling light beam passes alternately through the optical system. These two light beams are separated in time. When the sampling light beam is passed through, the sample is placed in the sample holder. When the reference beam is passed through, there is no sample in the holder. This procedure, therefore, is relatively cumbersome because of the need to change periodically the sample in the holder.

In another form of instrument, the incoming beam from the steady state source is split so that a small portion of the beam passes through a reference detector and upwards of 95% of the light beam passes through the sample and the detector associated with the sample. This system looks at the overall spectrum of the white light effect in determining the analysis of the sample.

These above known systems all have in common the use of the two light beams. The light measurement is of the entire white light spectrum or a particular wavelength.

Analysis to obtain a measurement of concentration of analyte is determined from a measurement of the absorbance of a chromophore which is given by the formula:

$$Abs = -\log \frac{I}{I_o}$$

I refers to the intensity measured through the sample and $I_o$ refers to the intensity of the reference beam. The intensities could be of either a white light measurement or of a particular wavelength as generated by the double beam method.

Absorbance is related to the chromophore's concentration in terms of the formula:

$$Abs = Ebc$$

where E is the extinction coefficient which is related to an absorbability factor; b is the path length of a cell; and c is the concentration.

A characteristic requirement of known systems using a single beam is that a very high stability of the operation of the light source is necessary in order to obtain measurements with the requisite degree of precision. For effectively precise measurements it is necessary to have a high light stability in the order of about 1/10% over 1 hour. Relatively costly technology and components must be used to obtain this stability. Because of this high degree of stability, a relatively high speed operational procedure and analysis system can be used. However, as indicated, this is costly because of the components and methodology needed to obtain the high degree of light stability.

With the increasing throughput load demands for precise analysis and measurement in the medical, chemical and quantitative fields, it is becoming important to provide for high speed measurements on system containing multiple samples with precision.

Currently known systems do not provide a fast enough throughput with sufficient precision, and at an acceptably relatively lower cost. There is a need to provide systems which can immediately provide analyses of multiple samples.

SUMMARY

The present invention seeks to meet the current needs

In terms of the present invention, a monobeam system is contemplated. The light source instability to obtain the same precision scale is relatively higher than in prior art systems, namely about 1% over about 15 minutes, the course of a chemical reaction. This increased instability permits for improved throughput at less expense. Highly effective results in precision are achieved by the invented flash correction techniques. Moreover, the speed with which the system operates, namely the interval between successive flashes, is in milliseconds whereas in the dual beam system or known single beam systems an output of the lamp is required to last for many seconds.

According to the invention the photometer to measure the changes of concentration in at least one chromophore substance uses a flash lamp and multiple wavelength flash correction methodology. The amount of absorbance for at least two, and preferably up to five, selected wavelengths is measured at each flash and the chromophore concentration is determined by an appropriate linear combination of the absorbance values. By this linear combination, fixed coefficients, k, dependent on a set of extinction coefficients, e, and a matrix of coefficients, f, representative of a noise pattern in the photometer is applied to the set of absorbance values.

The optimum linear combination which minimizes the effect of noise is ascertained for at least two different selected wavelengths, thereby reducing the amount of error in measuring the concentration. This optimum linear combination takes into account the nature of the correlations in errors at the various wavelengths and also the direction which the chemistry proceeds, namely that determined by the chemistry extinction coefficients.

In view of the millisecond flash rate of the light beam, which provides a higher intensity than the steady state lamp source, and the measuring means and flash correction technique of the invention, the overall invented system is not as sensitive from a stability viewpoint, and is faster in ultimate throughput. The intensity of the flash lamp is about 50,000 watts for about 1 to 5 microseconds of the flash. A throughput rate in the range of 1 sample about every 16 seconds is obtained with the invented analysis system.

Accordingly, instead of a white light steady lamp source as a reference signal, the present invention is directed to a high intensity flash lamp operable for short pulse duration, namely microseconds. Instead of effectively stabilizing the system with complex componentry, the monobeam flash system operates with a stability derived from employing an optimally selected linear combination of absorbance values for two or more wavelengths generated by the flashing light beam. A linear combination of absorbances is equivalent to the logarithm of the product of powers of intensity values at different wavelengths. The optimum linear combination effectively increases the signal effect and decreases the noise effect of the light source, namely, the flash lamp.

The approach adopted in the present invention increases the speed and throughput while retaining high precision by the use of a flashing lamp to generate the light beam as opposed to a steady state white light source. Additionally, since the lamp is not on all the time, it does not burn out quickly. There is no increase in costs because of downtime for replacement and recalibration. Also the heat generated is less. These factors also provide, therefore, for simpler systems with a higher throughput.

On the other hand, a flashing light source does provide problems, namely that the light flash is not identical each time. Accordingly, the amount and nature of light through the sample is different every flash. This problem, however, is remedied by the invention by employing at each flash the strong correlation in intensity variation at the different wavelengths.

The flashing white light lamp has varying intensity characteristics with each flash since the arc between the two electrodes generates variable energy. Moreover, the arc moves physically to different positions in the lamp, and thus the image shifts back and forth at the photo-detectors of the photoarray receiving light after having passed through the sample. Also, the optics associated with the arc can cause differing fractions of the energy to pass through a monochromator's input slit located downstream of the sample.

The invention employs highly correlated noise characteristics associated with each flash at the various wavelengths. This reduces the effect of the noise and thereby provides more accurate absorbance signals. This will provide more precise concentration values. The signal to noise ratio is maximized by selecting the optimum linear combination of absorbance values at two or more wavelengths as concentration estimate.

The monobeam system operates with simultaneous intensity measurements at different wavelengths. Accordingly, there is a reduced need for intensity stability in the light source as compared with prior art devices.

Beyond the application of measuring absorbance and hence the changes of concentration in a single chromophore, the system is sensitive, for example, to the existence of interfering substances such as lipids or hemoglobin in different samples When such substances are present, the system will accompany concentration results with information that interfering substances may have adversely affected these results.

The invention also covers a method for determining extinction coefficients for a chromophore substance up to an arbitrary multiplicative factor from absorbance measurements taken with changing amounts of that substance. This technique can also be used to verify that a given chemistry has only one significant chromophore present as the reaction proceeds.

With the photometer it is possible to select a set of five different wavelengths out of ten available wavelengths at which to measure absorbance values for any given chemistry. A set of five wavelengths, in many cases, permits optimal use of the absorbance values in obtaining an estimate for the chemistry's chromophore concentration. If desired, more or less than five wavelength output signals can be used. In other cases, a monochromator in the photometer can have more photoarray elements in the detector. The photometer includes detector openings, and the photoarray is selected to be in a spaced location for the different wavelengths.

The intensity signal at two or more wavelengths is obtained, and an electronic module processes analog intensities values to digital absorbance values. A microprocessor program combines these absorbance values in linear combinations to obtain chromophore concentrations.

The monochromator system includes means for dispersing the flashing light beam passing through the sample into multiple wavelengths directed to the detector openings.

The invention is further described with reference to the accompanying drawings.

DRAWINGS

DESCRIPTION

Photometer unit

Figure 1:
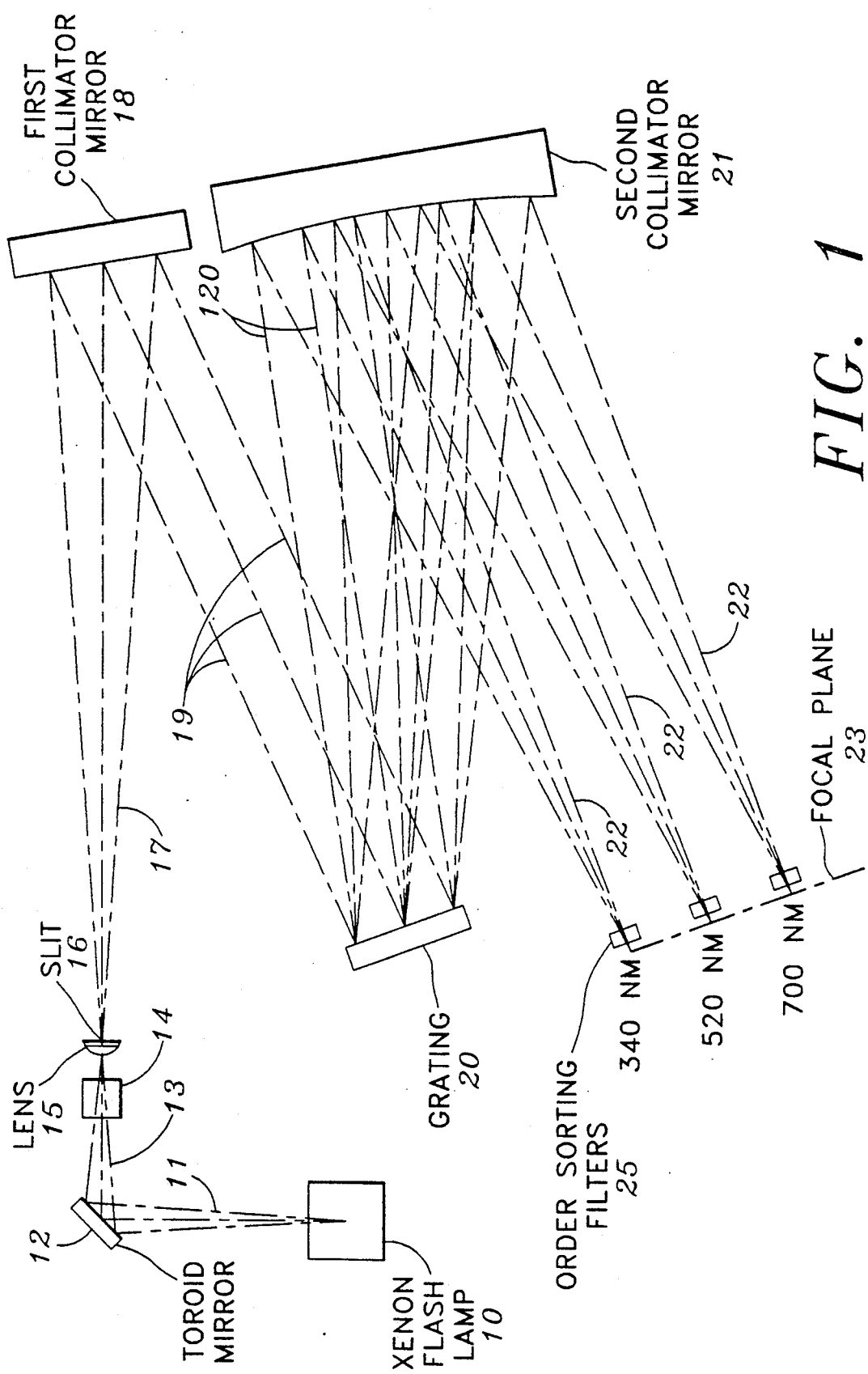
FIG. 1 is an optical diagram of a monochromator in accordance with the invention.
Figure 2:
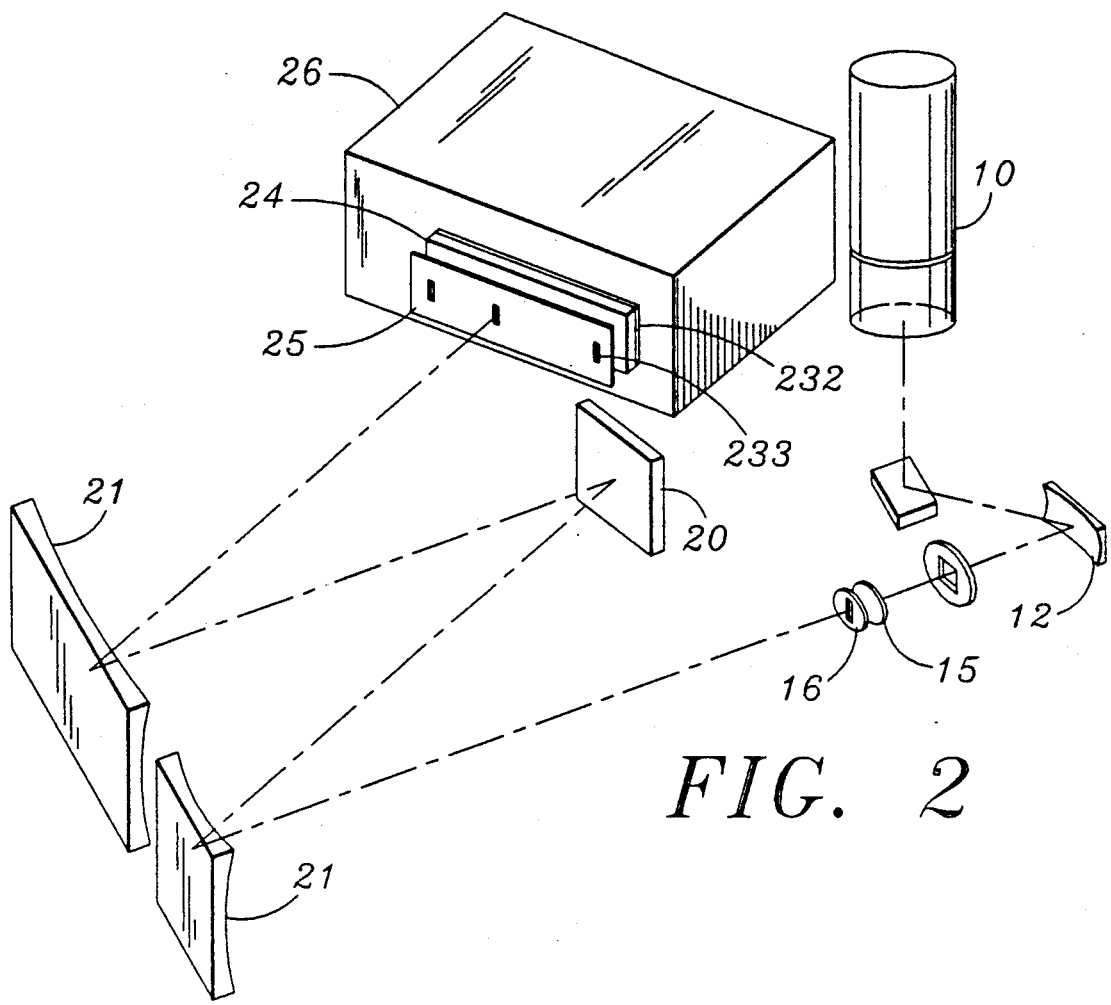
FIG. 2 is an diagrammatic illustration of the components of the photometer viewed isometrically.

A photometer includes a monochromator 204 and a flash lamp 10 together with detector means. The xenon flash lamp 10 is mounted to transmit a white light beam 11 in pulse form towards a toroid mirror 12 which reflects a beam 13 through a sample holder or cuvette 14. The cuvette 14 has a path length of about 5 mm for the light beam 13. After the passage through the cuvette 14, the light beam 13 is directed towards a lens 15 and from lens 15 the exiting light beam passes through a slit 16 as a diverging beam 17. This beam 17 is directed to a first collimator mirror 18. Reflected from the collimator mirror 18 are parallel light beams 19 directed to a diffraction grating 20.

From the diffraction grating 20, each element of the beam is dispersed or divided into representative multiple divergent further beams 120 directed to a second collimator mirror 21. The second collimator mirror 21 reflects the beams 120 into a converging beams 22 directed to a plane 23 representing discreet wavelengths of the beams 22 and where a detector array 24 is located. Ahead of the array 24 is an order sorting filter and slit array 25 which permits for discreet wavelengths, up to ten in number to pass to the detector 24. From the detector array 24 the intensity signals of the various wavelengths are transmitted to an electronic module 26 for measurement and processing with a microprocessor or in terms of control under a computer program.

The optical components are mounted in a housing 27, and the entire photometer unit which includes the electronic module 26 is part of a chemical analytical machine which includes means for locating and removing sample cuvettes 14 automatically into a location 28 in the housing 27 as appropriate. Suitable recording means is provided for setting out the data obtained from the electronic module 26.

Five different wavelengths are selected from ten available wavelengths for processing to determine absorbance values and hence concentration values. These values are determined in a manner such that signal to noise ratio is maintained at a maximum. Additionally, the extinction coefficients of each of the chemistries can be determined in a manner to be described. These wavelengths are, for instance, in the range of about 340 nm to 700 nm.

Determining the Linear Combination of Absorbance Values

Measured absorbance values during a reaction are the sum of three effects: (1) a given chemistry's principal chromophore whose concentration is to be determined, (2) various possible interfering substances, and (3) various kinds of error in absorbance measurement. In category (3) the effects due to flash lamp variation are of significance, and it is this variation and noise effect which is minimized.

An accurate estimate of a chemistry's principal chromophore concentration as it varies throughout the reaction is obtained in the face of the above interfering effects and the other kinds of errors. From this concentration data either endpoint values or rate values are derived. This in turn is used to determine the desired analyte concentration in the sample.

Interfering substances in category (2) can be of two types. First, there are interfering substances introduced from the sample which remain constant throughout the reaction. These are of concern to endpoint chemistries. Rate chemistries make use of time rates of absorbance change occurring as the reaction proceeds, and the presence of a constant offset from such an interfering substance does not affect the rate value obtained. The second type of interfering substance participates in the reaction and varies in concentration with that of the principal chromophore. This is of importance to both endpoint and rate chemistries.

Variations in the flash lamp 10 play a significant role in these errors because they are comparatively large. The absorbance variations at the various wavelengths are strongly correlated. This correlation makes it possible to reduce substantially the error in chromophore concentration estimates by properly adjusting the coefficients used in the estimates.

Different extinction coefficients express the relative amounts by which the absorbances change at various selected different wavelengths. The extinction coefficients amount to a sampling at the various selected different wavelengths of the substance's absorbance spectral curve. The extinction coefficients are used to arrive at a best estimate for chromophore concentration.

Errors in absorbance measurement can be characterized statistically by measuring the absorbance variations which occur with deionized water over a large number of samples. A covariance matrix, F, expresses the statistical relationships extracted from such a set of measurements.

An estimate used for the principal chromophore concentration is a particular linear combination of absorbances. Where $a_1, a_2, \ldots, a_n$ are the measured absorbances at n chosen wavelengths, then $k_1 a_1 + k_2 a_2 + \ldots + k_n a_n$ is the concentration estimate. The proper selection of the coefficients, $k_1, k_2, \ldots, k_n$ is then determined both by the chromophore's extinction coefficients and the above covariance matrix, F, with respect to the selected set of wavelengths.

In deriving $k_1, k_2, \ldots, k_n$ it is assumed that no interfering substances are present. Only the one chromophore and absorbance measurement errors need be considered. This strategy uses only the chromophore's extinction coefficients and the deionized water covariance matrix, F, to obtain a unique, optimum solution for the k-coefficients minimizing the mean square error made in the concentration estimate.

However, to provide for the possible presence of interfering substances, linear expressions are developed which measure the departure in various orthogonal directions of the measured absorbances from the assumed single-chromophore extinction coefficient direction. Taking the absorbance measurement error in each of these directions into account, a threshold is set for each expression. Should any threshold be exceeded, this indicates that interfering substances are present in excessive amounts and that the concentration estimates could be invalid.

In arriving at an optimum estimate of chromophore concentration, absorbance is assumed to be due to the single chromophore and to errors distributed according to the variation observed with deionized water. This is expressed as Beer's law, namely $$a = c \times e + f$$

where c is the scalar chromophore concentration and where a, e, and f are $n \times 1$ column matrixes of measured absorbance values, extinction coefficients of the chromophore, and errors in absorbance respectively.

The flash lamp 10 is used for measuring changes of concentration in a single chromophore substance, indicating the amount of a particular analyte present in a sample. This is done by measuring the amount of absorbance for up to five selected wavelengths at each flash. The chromophore concentration at each flash is then estimated by an appropriate linear combination of the absorbance values.

Should no errors be present, a great many different linear combinations could be used equally well, since the absorbance values at more than one wavelength for measuring the concentration of a single chromophore component constitutes redundant information. However, with the large amount of error present, caused mainly by variations in the lamp 10 from flash to flash, an optimum linear combination, which minimizes the effect of these variations on the concentration determination is needed.

The optimum linear combination is found using the correlations among errors at different wavelengths to reduce the amount of error present in the concentration estimate. The optimum linear combination reflects both the nature of the correlated errors and the "direction" in which the chemistry proceeds, namely, the chemistry's extinction coefficients.

Assuming that the absorbance measurements are properly offset the mean values of the errors f are zero. k is a $1 \times n$ row matrix consisting of the coefficients of the desired optimum linear combination. The linear combination, namely the matrix product $c_o = k \times a$ is an estimate of c. The statistically expected mean value E of this estimate is:

$$E\{c_o\} = E\{k \times a\} = c \times (k \times e) + k \times E\{f\} = c \times (k \times e)$$

To ensure that this estimate is the same as the actual value, c, the constraint $k \times e = 1$ is placed on k. Thus, the error in the estimate can be expressed as:

$$c_o - c = k \times f$$

The second condition placed on k is that the mean square error of this estimate is to be minimized. That is:

$$E\{(c_o-c)^2\} = E\{(k \times f)^2\} = E\{(k \times f) \times (k \times f)'\} = k \times E\{f \times f'\} \times k'$$

is to be a minimum, where the ' notation indicates matrix transpose. the $n \times n$ covariance matrix $E\{f \times f'\}$ is denoted by F.

Thus, given e and F, k is determined such that $k \times F \times k'$ is a minimum subject to $k \times e = 1$. Using a differential argument, at the minimum:

$$d(k \times F \times k') = 2 \, dk \times F \times k' = 0$$

whenever $$d(k \times e) = dk \times e = 0.$$

Hence $F \times k'$ and e must be parallel. That is, for some scalar, t, $$F \times k' = t \times e \text{ or } k = t \times e' \times F^{-1}$$

where $F^{-1}$ is the matrix inverse of F. Then requiring $k \times e = 1$ determines t. The final solution is:

$$k = (e' \times F^{-1} \times e)^{-1} \times e' \times F^{-1}.$$

Variances and covariances of f can be measured by observing the corresponding variances and covariances of absorbances occurring in a constant medium in the cuvettes such as air, deionized water or a dye. The set of covariances or variances of these absorbances about their mean values for all possible pairings of wavelengths constitute the matrix $F = E\{f \times f'\}$ for that wavelength set.

This calculation of F is performed during the lamp calibration process which is effected, for instance, when a new lamp 10 is inserted into the system, or a lamp 10 drifts, or alternatively a user defines a new chemistry for an existing system. Also during these procedures, the coefficient extinction e is retained constant, and k is calculated according to the algorithm:

$$k = (e' \times F^{-1} \times e)^{-1} \times e' \times F^{-1}$$

Figure 4:
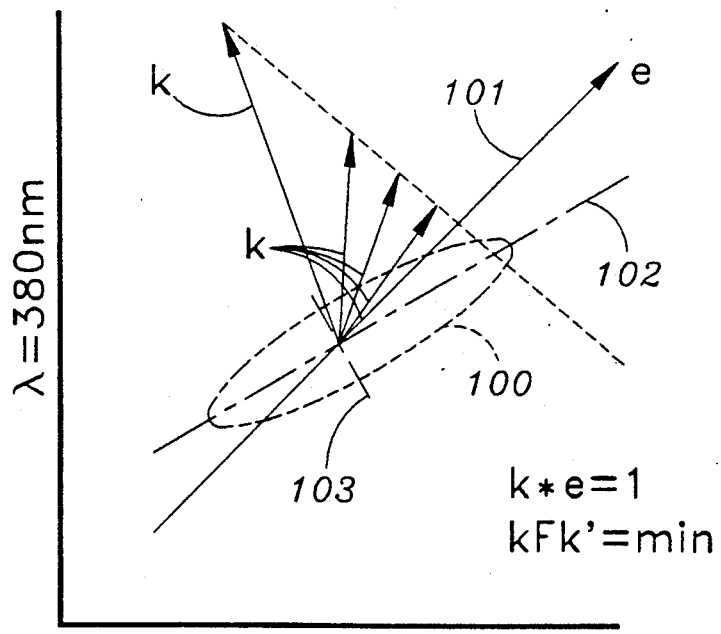
FIG. 4 is a graphical representation indicating an absorbance scatter plot, namely, the relationship of signal and noise at two selected wavelengths in a manner to obtain the optimum linear combination of absorbance values at these two wavelengths.
Figure 3:
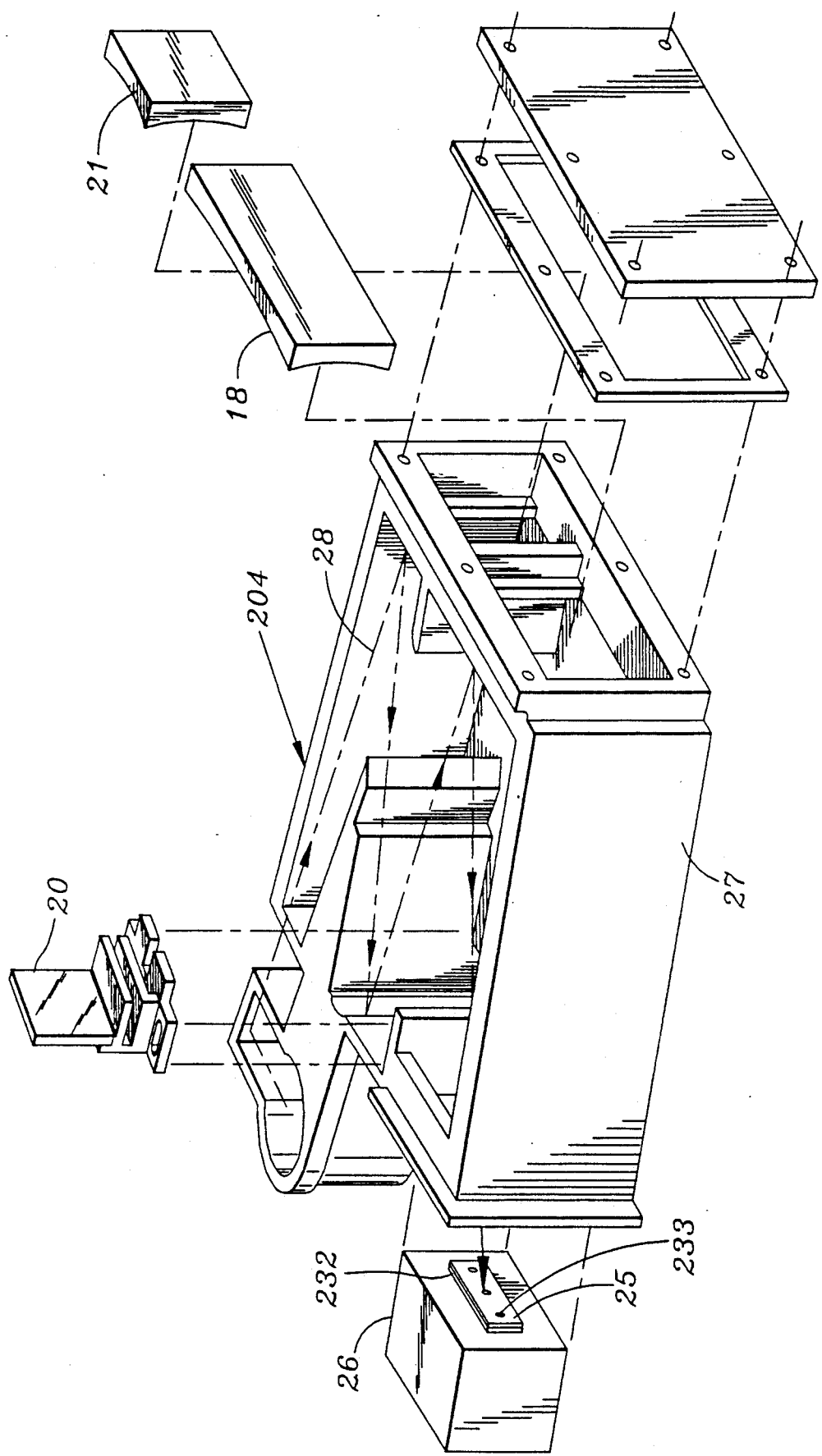
FIG. 3 is an isometric top exploded view of the monochromator housing with parts broken away.

In FIG. 4, a graphical vectorial representation of an absorbance scatter plot for two selected representative wavelengths 340 nm and 380 nm is depicted in the determination of the k value.

In reality, there are five wavelengths which are obtained from the ten wavelength monochromator 204. When five wavelengths are used, the two-dimensional graphical picture is effectively converted to a five-dimensional picture. The graphical shape 100 is representative of correlated noise and instead of having only two dimensions illustrated, has five dimensions according to the number of wavelengths being considered. The graphical signal line 101 indicates relative amounts of changing absorbance due to changing concentration of a chromophore in a sample.

In practice, noise is correlated as depicted by the elliptical representation 100, indicating a scatter plot of the two absorbances at 340 and 380 about their mean values. From this scatter plot is derived the F matrix of variances and covariances for these wavelengths.

The solution to obtain the best k value, namely, the length and direction, is governed by two mathematical expressions: Firstly, $k \times e = 1$ wherein e is the extinction coefficient of the chromophore. In the second expression, $k \times F \times k'$ is to be minimized. F is the covariance matrix of the noise, namely, it defines the noise 100. Axis 102 represents the length of the error distribution, and axis 103 represents the width of the error distribution.

The condition, $k \times e = 1$, is represented in FIG. 4 by having all the possible k vectors with their endpoints lying on the dashed line which is orthogonal to the extinction coefficient direction, e. The task is then to select from among all such vectors, k, satisfying this condition, that optimum k which c minimizes the mean square error, $k \times F \times k'$.

Determining the Extinction Coefficients of e

The technique used to find the extinction coefficients of a chromophore of a given chemistry at a particular set of wavelengths is a generalization on Deming's method of finding best linear fits to noisy data.

A covariance matrix G is determined by observing variations of absorbances about their means in the various pairings for the set of wavelengths. These observations are made while the chemistry's chromophore is changing in the cuvette. The matrix G therefore reflects the relative amounts by which the absorbances change at these wavelengths, as well as the errors characterized by F. The relative extinction coefficients are obtained from G without allowing skewing from the F-type errors.

First, F is subjected to an eigenvector analysis. A unitary transformation, U, is found which rotates the system of absorbance coordinates to these eigenvectors. A second transformation, V, is found whose matrix consists only of diagonal elements and with the diagonal elements being the square roots of the eigenvalues. This, together with U, has the effect of transforming F into an identity matrix, $F'' = VUFU'V' = I$. G is then transformed by the same transformation, $G'' = VUGU'V'$, and subjected to another eigenvector analysis. The eigenvalues of this latter matrix should consist of one large value for the chemistry variation and all other values near unity from errors indicated by F.

With the original data values which determined G transformed by VU, their covariance matrix would be just G″. Deming's method is used to obtain a best fitting line which minimizes the mean square orthogonal distance of these transformed points to the line. The line direction is the above eigenvector of G″ with the large eigenvalue. The elements of e are then found by transforming this eigenvector back to the original absorbance coordinate system.

This method also makes possible a check on the purity of the chromophore being measured. Should more than one eigenvalue of G″ be found to lie substantially above unity, this indicates the presence of other changing chromophores.

These extinction coefficient values are only relative values since no concentration information has been involved.

Electronic Module and Processing

The circuitry in the electronic module to process the intensity signals at different wavelengths is now described.

Figures 5, 5A:
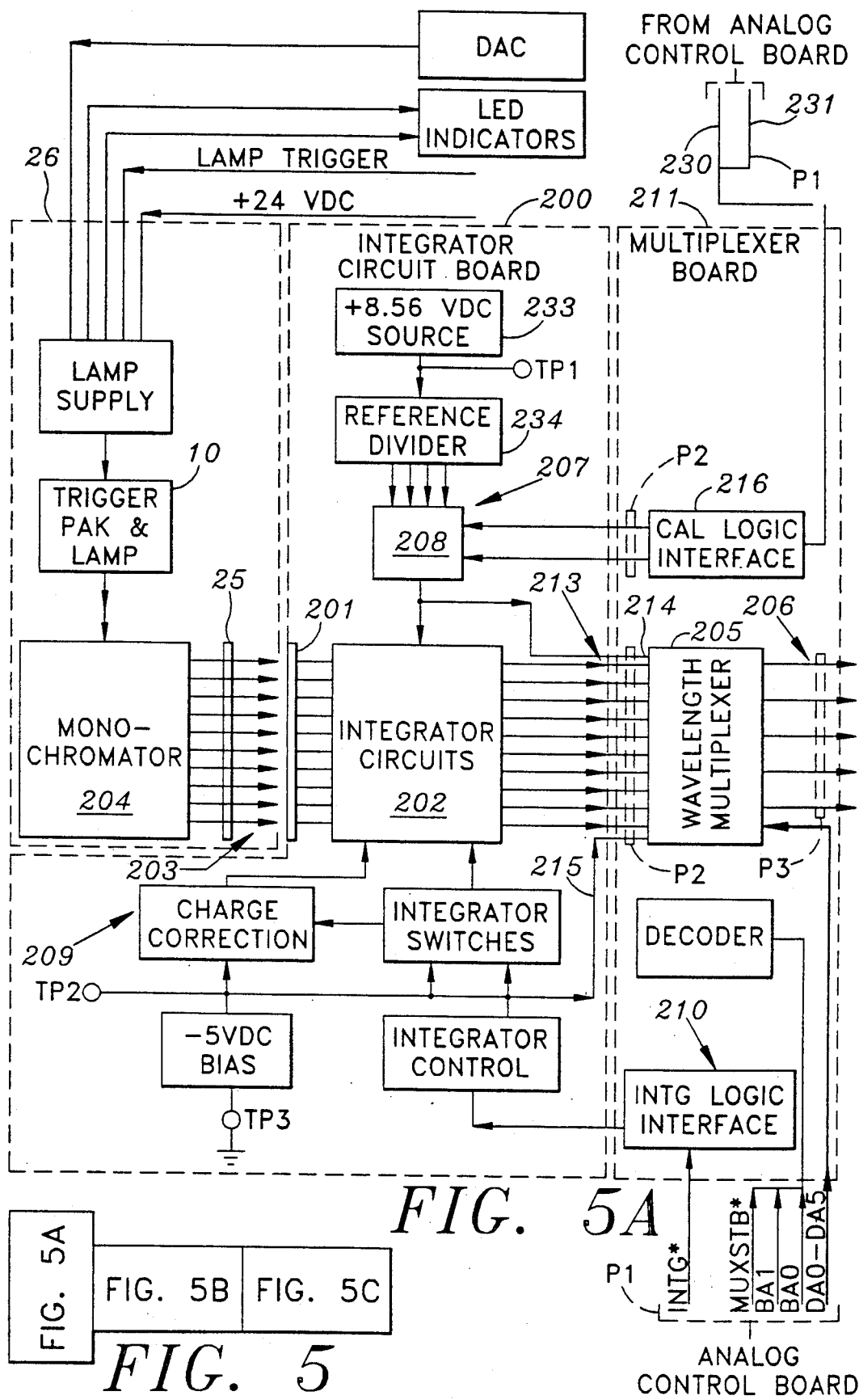
FIGS. 5a, 5b and 5c are block diagrams representing the electronic module associated with the detector of the photometer.
Figure 5B:
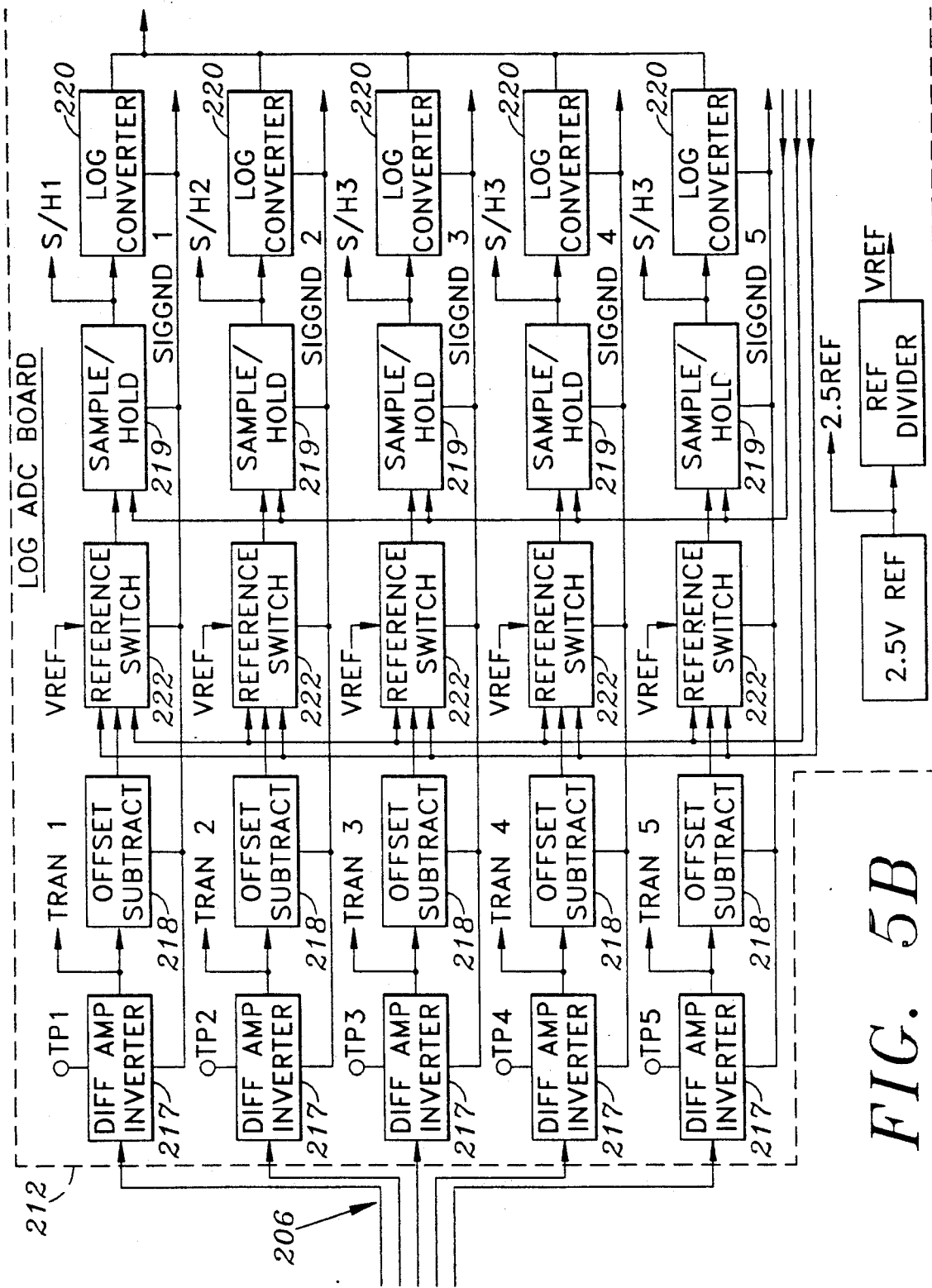
Figure 5C:
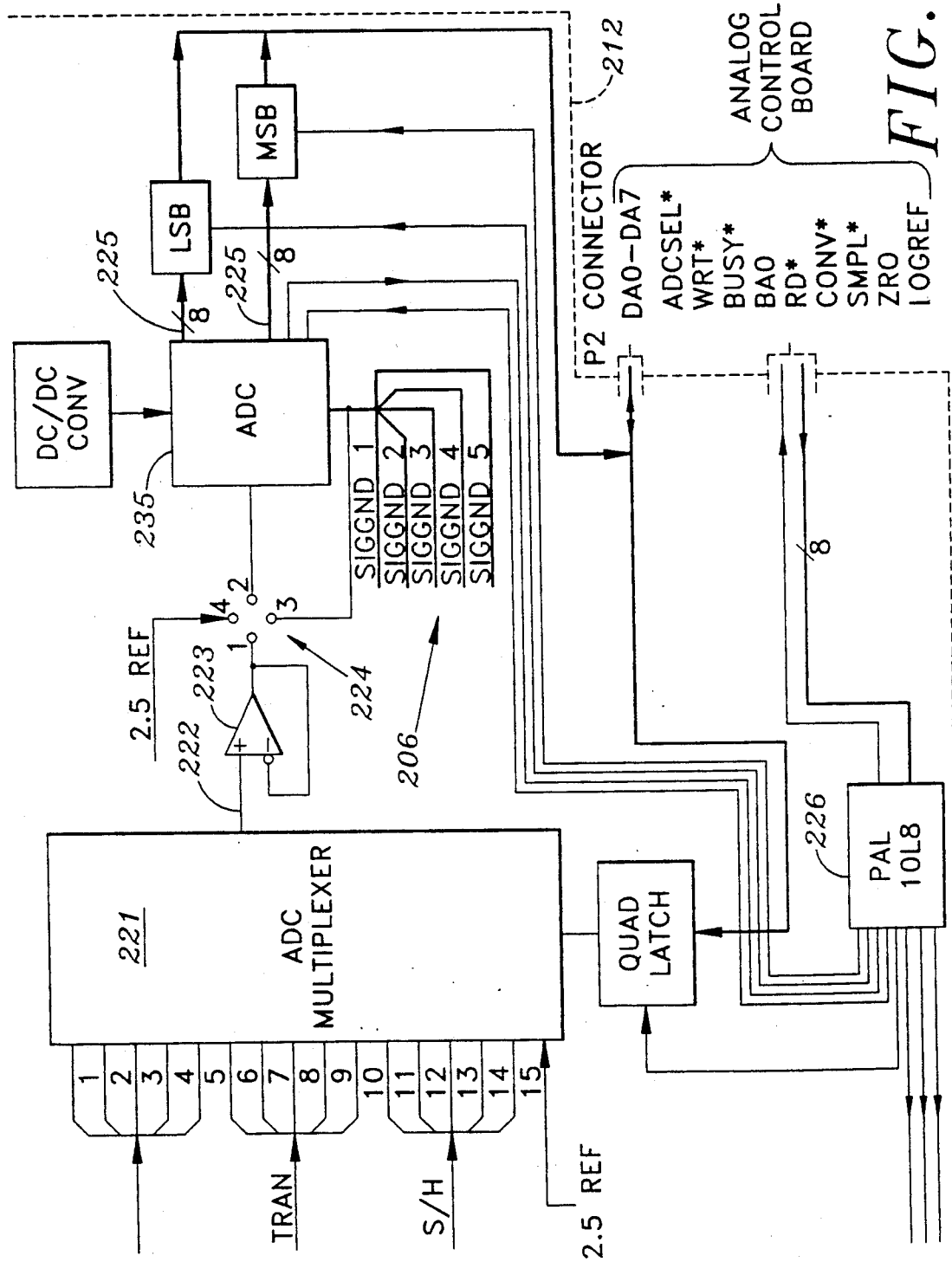

FIG. 5a shows the photometer assembly integrator circuit board and wavelength multiplexer board in block form. FIGS. 5b and 5c illustrate a block diagram representation of the log ADC, namely, log/analog digital circuit board.

Integrator Circuit Board 200

The functional requirements and the mechanical requirements for the optical detector includes an integrator circuit board 200 consisting of a ten sensor optical detector assembly 201, ten integrator circuits 202, associated logic control circuit 210, and a calibrator circuit 207. The optical detector circuits measure pulsed light input 203 from the monochromator 204 and convert energy pulses to an electrical signal proportional to the time integral of the current pulse.

A photodiode assembly 232 of the detector assembly 201 is soldered to an electronic assembly module 26, which is mounted to the monochromator assembly 27. The detector 201 mounts directly against a ten slit mask plate order sorting filter 25. Each slit 233 in the mask acts as a 5 nm bandpass filter aligned at a specific center wavelength within the light spectrum from 340 nm (nanometers) to 700 nm. Each photodiode sensor is aligned with a specific slit 232 of the mask. The photodiode signal current is proportional to the intensity of the external light source.

Each photodiode is connected to a precision integrator circuit 202 to measure the total light energy, namely the time integral, of the transmitted light pulse. All integrator circuits 202 are switched ON in parallel measuring single pulse energy at each wavelength.

Output signals from the ten circuits 202 are connected to a wavelength multiplexer assembly 205. This multiplexer circuit 205 provides the capability of selecting five signals 206 from the ten integrator circuits for additional signal processing.

Integrator circuit gain, that is sensitivity, differs for each wavelength, and is dependent on the composite characteristics of the detector spectral responsivity, the xenon flash lamp 10 spectral intensity curve, and the monochromator transmittance. Integrator capacitor values for the various circuits are selected to compensate for the overall variations in signal transmittance.

Each signal channel provides a 0 to −10 volt output directly proportional to the time integral of the input current pulse. The integrator capacitor value determines the circuit sensitivity, and the capacitor values, or circuit sensitivities, are based on the complete optics system, the detector assembly 201 and the flash lamp 10.

The energy from lamp 10 varies flash to flash, with average signal levels controlled by adjustment of the lamp supply voltage. The output signal at the various wavelengths should fall within the signal range of −7.0 to −10.0 volts. Lamp flashes occur at a nominal rate of 120 pps (pulses per second), and the light pulse width is approximately 1.5 usec. Each detector acts as a current source while exposed to light, and as an open circuit (high impedance) during dark intervals.

A programmable calibration circuit 207 provides three levels of signal current for measuring integrator sensitivity and signal range. These signals are used for linearity calibration during system linearity tests, and are used for diagnostics tests in both system and assembly tests.

The calibration circuit 207 consists of the regulated reference source 233, a precision divider network 234, and the four input multiplexer 208. The voltage source is derived from a programmable 2.5 volt shunt regulator, with an output connected to three resistors in the divider network 234. Divider outputs are 0,.01,.1 and 1.0 ratio of the full reference voltage.

Calibration signals are capacitively coupled to each integrator circuit 202, coupled through a capacitor matched in value to the integrator capacitor used in each circuit. This results in an output voltage nominally equal to the step voltage generated by the reference source 233.

Calibration signals are derived from a regulated DC voltage source 233 of +8.56 VDC. A test point TP1 is provided for monitoring the reference voltage. Calibration signals are generated by switching the output of a four input multiplexer 208 from ground to one of three DC voltages. A one of four decoder, internal to the multiplexer, decodes a two line binary code to select the programmed calibration step. Two external latched address lines are required to control the multiplexer. Address lines 230 and 231 are routed from a connector P2 and are driven by open collector inverters. The multiplexer 208 is a CMOS device operating from the +15 VDC supply. Logic lines are terminated with 4.7 K pull up resistors.

Each sensor in the detector 201 provides a current input to a high speed precision integrator circuit. The circuit 202 consists of a high speed, low bias current (3 pa max), low offset voltage amplifier; a high stability low loss integrator capacitor, and a JFET/analog switch discharge circuit.

A two switch discharge circuit is used in the integrator RESET circuit to reduce the summing junction leakage currents during signal integration interval. During the integration time, both switches are OFF, JFET switch is biased off, and the analog switch is open. The output signal is applied across the two switch network between the amplifier output and the summing junction.

To reduce the summing junction leakage current, a 750 ohm resistor is connected between the two switches and ground providing a low impedance path to ground for leakage currents from the analog switch. This reduces the JFET drain to source voltage to a few millivolts, greatly reducing the summing junction error current.

JFET switches are switched OFF by switching the gate voltage to a 5 VDC bias source. All analog switches are "closed" with a logic true (high) input signal. Coincident, complementary signals required for driving the circuits are derived from the "Q" and "Q*" outputs of a transparent latch. Two analog switches and one JFET switch are used in each integrator circuit. The JFET switch and one analog switch are used in the integrator RESET, namely capacitor discharge, path. The second analog switch applies a negative bias to the JFET gate junction during the integrating interval. All circuits are switched in parallel, controlled by the single input line INTEG. Integration time is under software control, normally ON for several milliseconds.

Under typical system operation, the integrator circuits 202 are switched ON, the integrator offset is measured, the lamp 10 flashed and the signal levels measured and held. Approximately 110 usec following the lamp flash, the signal levels are sampled and processed. Integrator circuits 202 may be reset after sampling; however, integrators are normally reset approximately 3 milliseconds after the lamp flash.

The capacitor values are selected to provide approximately equal signal out at all wavelengths with a xenon flash lamp source 10, monochromator assembly 204, and glass cuvette 14 filled with deionized water.

Analog signal outputs from the integrator circuits 202 are routed to the multiplexer interface connector P2 to provide multiple inputs to the wavelength multiplexer circuit 205.

JFET switches inject a charge error when the integrators 202 are switched ON. The negative change at the JFET gate junction is coupled to the integrator summing junction through the gate to drain capacitance. This charge error results in a positive output offset error. The error voltage is inversely proportional to the integrator capacitor value.

Charge compensation is accomplished by coupling a positive voltage step change to the integrator summing junction through a 12 pf capacitor. During the integrator RESET interval, the coupling capacitor charges to a negative voltage determined by the adjustment setting. When the integrators 202 are switched ON, the capacitor is switched to ground transferring the capacitor charge to the summing junction. The coupling capacitor remains grounded during the integrating interval and recharges during RESET. Compensation delay is accomplished by a single transistor switch delay time and analog switch propagation delay time.

Each integrator circuit, 202, requires two coincident complementary logic signals for enabling and resetting the circuit. All integrators are switched in parallel, driven from the "Q" and "Q*" outputs of a single quad "D" latch. Latch inputs are connected common, driven by an open collector invertor on a multiplexer board 211.

All logic circuit drivers are latched circuits; all drivers open collector outputs. Two circuits require interfacing with CMOS components, and one driver interfaces with TTL circuitry.

All integrator analog outputs, and ten OPAMP outputs, are connected to connector P2 for interfacing with the multiplexer circuit 205. Five analog SIGGND lines 206 are routed to connector P3. Analog signals are routed to the multiplexer circuit and five of the signals are rerouted back to the Integrator Circuit Board 200 to connector P3.

Multiplexer Board 211.

The wavelength signal multiplexer circuit 211 provides the means for addressing five analog signals 206 derived from preamp integrator circuits 202 or preamp calibration circuits. Wavelength analog signals are cross connected to five multiplexers 205 to provide program selection of various signal combinations as determined by system requirements. Calibration signals are connected to each multiplexer 205 to provide diagnostic test signals.

The board 211 connects to the preamp integrator circuit 202 through an interface connector. All logic address and data lines interface directly to the multiplexer board 211 through connector P1. All logic decoding and data bus latches are included in the board. Analog output signals are interfaced directly to the Integrator Circuit Board 200. Output signals normally connect to unit gain difference amplifiers 217 on the LOG/ADC conversion board 212.

Open collector drivers provide interfacing TTL inputs to CMOS circuits on the Integrator Circuit Board 200. Five wavelength signals can be addressed for each chemistry test, one from each of the multiplexers 205. Certain preferred wavelengths are specified for most of the chemistry measurements. Final wavelength selection is be defined by the system program.

Each of the five multiplexers 205 require a three bit binary address to select one of eight input signals. The total of fifteen address lines are derived from three "D" hex latches. The multiplexer circuit 205 consists of five analog multiplexer chips, each with an internal one of eight decoder. Analog inputs are in the range from +10 VDC to −10 VDC.

Ten input analog signals from the Integrator Circuit Board 200 are interconnected to the five multiplexer chips 205. Six inputs of each multiplexer 205 are derived from the ten input signals 213. The two remaining inputs 214 and 215 are connected to reference voltages for diagnostics tests. Interconnection of the analog inputs provides a means for monitoring various combinations of signal information as required for a specific chemistry test.

Analog signals to input 214 are derived from a programmable calibration circuit 207 on the Integrator Circuit Board 200. This signal is controlled by programming the calibrator multiplexer 208 located on the Integrator Circuit Board 200. The multiplexer 208 is controlled by the two data bit lines 230 and 231. Input 215 is normally connected to a fixed −5 VDC reference source located on the Integrator Circuit Board 200. A TTL to CMOS interface 216 is required for the two control signals 230 and 231. An open collector hex invertor provides the interface circuits for all control signals to the Integrator Circuit Board 200.

Log/ADC Board 212

The log/ADC board 212 is designed to interface with standard TTL logic circuits. Analog inputs are designed for differential input signals driven from operational amplifier outputs. Analog signal lines are connected to the differential amplifier inverting input terminals; non-inverting lines are connected to the signal reference grounds.

Analog inputs are designed for +10 volt to −10 volt signals. Input signals can exceed 10 volts since operational amplifier outputs limit at approximately 13 volts operating from 15 volt supplies. The assembly is designed to monitor signals within the 10 volt range. Log circuits are scaled to accept 11.5 volts maximum input. Transmittance measurements are limited to 10 volts, which is the ADC full scale signal.

All control lines interface with a Programmable Array Logic chip. Input impedance for each line is one TTL gate. Terminating resistor networks are not supplied on the board. All data bus lines interface with tri-state bus drivers, and one TTL quad latch. All logic are driven from latched I/O sources.

FIG. 5b shows a block diagram of the circuit board 212. The LOG/ADC board 212 consists of five identical log conversion signal channels. Each channel consists of an input different amplifier 217, auto-zero circuit 218, sample/hold amplifier 219 and log converter circuit 220.

Output signals from the log converter circuits 220 are connected to a sixteen input multiplexer 221 for analog to digital conversion 5c. Signal grounds for each channel are isolated from analog and logic power ground. Signal grounds and AC analog ground are connected common at a star ground point. Logic ground is isolated from signal and analog ground paths, but referenced common at one point.

Signal inputs to each channel are connected to difference amplifiers 217 designed as unity gain inverters with common mode rejection of analog power ground noise. Signals from the difference amplifiers 217 are connected to test jacks for external test monitoring and to the ADC multiplexer 221 for diagnostics tests and lamp source evaluation. Amplifier outputs are directly connected to the auto-zero offset subtract circuits 218 to correct for dark signal offset and amplifier offset voltages. Reference switches select the auto-zero outputs or a DC reference voltage as the inputs to the sample/hold circuits 219.

A DC reference voltage is provided as a stand-by input to the log converter circuits 220, or the signal may be used for diagnostic tests. The sample/hold circuits 219 provide a constant signal to the log converter circuits 210, or the signal may be used for diagnostics tests. The sample/hold circuits 219 provide a constant signal to the log circuits during the log conversion and data read time. The sample/hold signals are also connected to the ADC multiplexer 221 for diagnostics monitoring.

Log signal outputs are connected directly to the ADC multiplexer 221. The multiplexer output 220 is connected to a voltage follower 223 which drives an input to a ADC 235. The ADC converter 235 provides latched sixteen bit output, in twos complement format.

Analog inputs to each channel are connected to unit gain difference amplifiers 217, connected as invertor circuits. A precision thin film resistor network consisting of four matched 50K resistors provides the matched resistor pairs required for 50 db common mode noise rejection.

Analog inputs are connected with the signal lead connected to the inverting input, and signal ground connected to the non-inverting input. The non-inverting input divider is referenced to the log channel signal ground. The circuit is designed for a minimum of 50 db common mode rejection of voltage difference between grounds.

PREAMP wavelength signals are of negative polarity. Log converter circuits require a positive input current; therefore, signal inverters are required. Diagnostic signals from the PREAMP are both positive and negative polarity; therefore, the invertor circuits 217 are designed for input signals in the range from +10 volts to −10 volts.

Invertor outputs are routed to test jacks for test monitoring, to the ADC multiplexer 221 for diagnostics, and to the auto-zero inputs.

Auto-zero offset subtracting circuits 218 provide for subtraction of offset voltages due to dark signal offset and invertor amplifier 217 offset. The circuit 218 consists of a low hysteresis storage capacitor driven by the invertor amplifier 218. The capacitor is switched to ground during the offset charging interval, and to the reference switch for offset subtraction. When switched to ground, the capacitor charges to a voltage equal to the input signal, normally less than 15 mv. The capacitor charges to a voltage equal to the input signal plus amplifier offset. The capacitor is grounded for a minimum of 600 usec to allow the capacitor to charge to full offset voltage. The capacitor is then switched "in series" with the invertor 218 output to subtract offset error from the total input signal.

Auto-zero charging time is software controlled and may vary from 600 usec to 2.0 ms in the instrument system. A 10 usec delay is allowed between switching the auto-zero charge cycle OFF and applying input signals.

Auto-zero switching is controlled by both ZRO and LOGREF control lines. With LOGREF switched low, capacitor switching is controlled by the ZRO line; grounded for ZRO high, and connected for the "difference" state with ZRO low (0). With LOGREF switched high, AZRO is forced high and the capacitor is switched to ground. The capacitor grounding path is completed through one analog switch circuit of Reference switches 222.

The sample and hold input signal is determined by the setting of the Reference switches 222. Either of two signal sources may be routed to the sample/hold circuits 219. Reference switches 222 are dual single pole double throw switches connected to route either the reference voltage or auto-zero outputs to the sample/hold circuits 219. One switch is controlled by the LOGREF logic line, the second switch controlled by AZRO. The reference voltage is set to provide log input current slightly greater than the log reference current. This results in a small negative voltage out of the log circuits.

Sample and hold circuits 219 for each log converter 220 provide a constant input current during the relatively long conversion and data read time. In the "sample" state, output signals track inputs and track any change in input signal. The input signal seen by the sample/hold circuits 219 is the difference between the total input signal and the voltage on the auto-zero capacitor.

Low level signal measurement and long log conversion time requires that the sample/hold circuits 219 are low drift circuits. For low level signals log circuit gain is high, and therefore drift is amplified during the long data conversion interval. The larger value capacitor reduces drift to the required rate, however increases acquisition time. Minimum sample time is 50 usec to allow for acquisition to within 0.1% of full signal.

During long data wait intervals, the sample/hold circuits 219 are switched to the "sample" state and LOGREF signal is switched ON. This provides a fixed stand-by current to the log converter circuits 220 preventing log circuit saturation.

Sample/hold circuits 219 are switched in parallel, controlled by the SMPL line. SMPL low switches all circuits to the "sample" state, and switched high sets all circuits to the "hold" state. Hold time may be as long as 5 ms in normal system operation.

Offset adjustments are provided for each sample/hold circuit 219 to correct for log converter input offset voltage error. The offset adjustments provide a means for adding an error voltage to compensate for the log circuit error. Linearity adjustments are set with precision step voltages.

Log converter circuits 220 provide an analog output voltage proportional to the logarithm of the input current. Log converters 220 require a reference current set to define the input current for zero output volts. The log converter circuits 220 are scaled at 7.62 volts per decade of input current, and the log chips are designed for a positive input current. The circuits are designed for a voltage input. Output signals are buffered using a buffer amplifier built into the chip. Outputs are connected directly to the ADC multiplexer 221 for digital processing.

The multiplexer 221 is a sixteen channel device which provides means for sequentially or randomly monitoring one of sixteen input voltages from various signal or diagnostics points. The multiplexer output 222 is connected to the high input impedance voltage follower 223 to reduce loading on input signal sources. The follower 223 output impedance is low to prevent ADC measurement errors. The follower drives the ADC 235 input impedance of 10K.

The multiplexer 221 requires a four line binary code, derived from external data latches. Decoders for selecting one of sixteen channels are internal to the multiplexer 221.

A 25 usec delay time is allowed for multiplexing and signal transient settling time. This means that data read should be delayed 25 usec after the multiplexer clock pulse. Multiplexer 221 inputs can be addressed in any order as required for the specific application. During normal system operation, absorbance readings are determined by monitoring only the log signals. During diagnostics tests, all signals can be monitored.

Multiplexer 221 inputs are grouped in two basic catagories: log converted signals for absorbance measurements, and diagnostics signals and the first five inputs are the log converter signals, and the next five inputs are transmittance signals and/or PREAMP diagnostics signals. The third group of five signals are diagnostics signals derived from the sample/hold 21- outputs. The last input is the 2.5 volt referencevoltage source.

The ADC converter 235 is a sixteen bit, successive approximation converter, with maximum conversion time of 35 usec. A precision +10 VDC reference source, internal to the ADC 235, is strapped to the internal DAC. The ADC 235 input impedance is strapped for 10 K ohms; full-scale input +/−10 VDC. The input pin can be jumpered to one of three signal sources 224: (1) analog ground, (2) +2.5 vdc reference, and (3) the multiplexer 221 output. The analog ground connection is jumpered to the input for zero adjustment. The 2.5 volt reference is connected to a pin, which can be jumpered to the ADC input for diagnostics tests. The ADC input is normally jumpered to the multiplexer 221 output.

ADC output 225 is latched sixteen bit data, in two's complement format. Previous data remains latched until the next data conversion pulse. A status line is provided to indicate that the ADC 235 is in a conversion cycle.

End of conversion is determined by monitoring the status signal, and detecting the trailing edge transition. An invertor, one gate of the chip 22 drives the output signal line. The "end of convert" pulse (BUSY) is a negative going signal, and the end of conversion is indicated by the trailing edge positive transition.

The sixteen data lines are connected to two eight bit, tri-state buffers. Data is read in two bytes, either byte may be read first as required by the system program.

Operation

With the apparatus, system and method of the invention, it is possible to determine concentration data of an analyte in a sample in a manner more precise and with greater efficiency than has previously been possible. A suitable program operates with the electronics in terms of the description provided to permit for the requisite data determination.

The output from the electronic module as absorbance values in a digital form is directed as raw absorbance values to a central processing unit which operates under a program to calculate the linear combination. The constants e, f and k are determined and the raw absorbance values are developed into scaled absorbance values. The next step is to apply a polychrome matrix, which used e and k to determine the matrix, for developing a particular scaled absorbance set. The estimated concentration using the k coefficients is obtained by the linear combination. Expressions for the presence of interfering substances are also obtained.

A second central processing unit operates on the concentration expression to smooth and interpolate data and develop lines of regression in specified data windows, thereby obtaining information such as the mean value of data in the window and the slope of data in the window.

While specific examples have been described, it will be understood that many variations are possible each differing from the other in matters of detail only. For instance, although the linear combinations have been described with reference to five wavelengths, it is possible to apply the same principles to either smaller or larger sets of wavelengths. This, for instance, could be 2, 3 or 4, 6, 7 or 8, or sets of several hundred wavelengths. For a system generating, say 128 wavelengths, 10 wavelengths can be selected for the linear combination. Also, although the description is concerned with the concentration of a single chromophore substance, the concentration of more than one chromophore substance within a given sample could be determined.

The invention should be considered as being defined by the following claims.

We claim:

1. A method of measuring the concentration of at least one chromophore substance in a sample comprising:
  (a) flashing a lamp to generate a flashing light beam to pass through the sample containing the chromophore substance;
  (b) measuring absorbance values by the sample at different wavelengths;
  (c) determining the absorbance values at the different wavelengths thereby to obtain a measure of the chromophore concentration; and
  (d) wherein errors in absorbance values are mutually correlated at different wavelengths, and the linear combination of the absorbance values at different wavelengths is determined in terms of this correlation.

2. A method as claimed in claim 1 including determining changes in the concentration.

3. A method as claimed in claim 1 wherein the linear combination reflects the nature of correlated errors and the direction of extinction coefficients of a chromophore in the sample, and including measuring changes in the chromophore concentration.

4. A method as claimed in claim 3 including measuring the absorbance values for about five different wavelengths.

5. A method as claimed in claim 3 including:
(a) ascertaining the concentration by applying Beer's Law in the formulation of $a = c \times e + f$ where a is a column matrix of absorbance values, c is a scalar chromophore concentration, e is a column matrix of extinction coefficients of the chromophores, and f is a column matrix representing errors;
(b) determining the linear combination according to constraints of $k \times e = 1$ and the noise represented by $k \times F \times k'$ as a mean square error being a minimum where k is a row matrix consisting of the coefficients of the linear combination, F is a covariance error matrix of f, and k' is the matrix transpose of k; and
(c) determining constituents of k according to the formula $k = (3' \times F^{-1} \times e)^{-1} \times e' \times F^{-1}$, wherein e' is the matrix transpose of e and $F^{-1}$ is the matrix inverse of F.

6. A method as claimed in claim 5, wherein the error matrix F is determined by measuring absorbance level variables from a flashing light passing through a constant medium.

7. A method as claimed in claim 6 wherein the error matrix F is measured for different combinations of pairs of wavelengths.

8. A method as claimed in claim 7 wherein the different combinations are obtained from sets of five wavelengths.

9. A method as claimed in claim 5 wherein the extinction coefficients e are determined for the chromophore of the selected chemistry reaction using a generalization of Deming's method and eigenvector transformations in order to obtain the best linear fit to the absorbance values.

10. A method as claimed in claim 9 wherein the determination of the extinction coefficient includes:
(a) determining a covariance matrix G by observing variations of absorbance level about their means for pairs of wavelengths, the variations being determined during the change of the chromophore concentration of a chemistry of the sample through which the lamp flashes, whereby the matrix G reflects the relative amounts by which absorbance levels change at the pairs of wavelengths in addition to the errors characterized by the matrix F; and
(b) removing data representative of the matrix errors thereby to obtain the relative extinction coefficients from the matrix G.

11. A method as claimed in claim 10 including subjecting the matrix F to an eigenvector analysis, obtaining a unitary transformation to transform the coordinates into the eigenvector coordinates thereby to carry absorbance levels over to eigenvector coordinates, obtaining a secondary transformation whose matrix contains only diagonal elements, and wherein the diagonal elements are the square roots of the eigenvector coordinates.

12. A method as claimed in claim 10 wherein the covariance matrix G is transformed by a unitary transformation and a secondary transformation, determining the eigenvectors and values of the transformed covariance matrix G, obtaining the best fitting line minimizing the mean square orthogonal distance of the transformed points to the line according to Deming's method, transforming the eigenvector back to the original absorbance coordinates system, and obtaining the elements of the extinction coefficient e.

13. A method as claimed in claim 9 including determining changes in the concentration.

14. A monobeam system of determining the concentration of at least one chromophore substance in a sample comprising a lamp for flashing a light beam through the sample, means for dispersing the light beam passing through the sample into multiple wavelengths, means for obtaining the intensity of the signal of the light beam at selected multiple wavelengths, means for determining from the intensity values the absorbance values as different wave-lengths, and means for determining the absorbance values at two or more wavelengths thereby to obtain a measure of the chromophore concentration, and including a monochromator for dispersing the light beam from a flash lamp, a lens for diverging the light beam from the flash lamp, the monochromator including a first collimator mirror for developing, from the diverging beam, a collimated beam directed towards a diffraction grating, the grating dispersing the collimated beam according to wavelength, a second collimator mirror receiving the multiple beams and reflecting the multiple beams into convergent beams at selected positions at a plane, the plane being located at a preselected plane for different wavelengths of the convergent beams.

15. A system as claimed in claim 14 including order sorting filters located at about the preselected plane.

16. A system as claimed in claim 15 including a toroid mirror for directing the light beam from the flash lamp through a sample holder, a slit located in close adjacency with the lens such that a selected portion of the light beam passes through the slit and is directed to the first collimator mirror.

17. A system as claimed in claim 16 including a detector photoarray at the preselected plane to receive a beam of at least ten different wavelengths, a slit array located ahead of the detector photoarray such that selected different wavelengths of the beam pass to the detector photoarray.

18. A system as claimed in claim 16 including an electronic module operationally connected with the detector photoarray thereby to receive in analog form the intensity signal of selected wavelengths of the beam, means for processing the analog intensity signals to obtain digital absorbance data such data being related to the intensity signals, processor means for processing the digital data to obtain a linear combination of absorbance values at the different wavelengths, and processor means for determining consequent concentration values from the absorbance values.

19. A system as claimed in claim 14 means for determining changes in the concentration.

20. A system as claimed in claim 18 including means for determining concentration changes.

21. A method of determining absorbance values at different wavelengths of a light beam passing through a sample chromophore substance in a sample comprising:
   (a) flashing a lamp to generate a flashing light beam to pass through the sample containing the chromophore substance; and
   (b) measuring the absorbance values by the sample at different wavelengths, wherein errors in absorbance values are determined at different wavelengths; and wherein a linear combination of the absorbance values reflects the nature of correlated errors and the direction of extinction coefficients of a chromophore in the sample.

22. A method as claimed in claim 21 including measuring the absorbance values for about five different wavelengths.

23. A method of determining the concentration of at least one chromophore substance in a sample in a monobeam system comprising flashing a light beam through the sample, dispersing the light beam passing through the sample into multiple wavelengths, obtaining the intensity of the signal of the light beam at selected multiple wave-lengths, determining from the intensity values the absorbance values at different wavelengths, and determining absorbance values at two or more wavelengths thereby to obtain a measure of the chromophore concentration, and including diverging the light beam from the flash lamp, directing the diverging light beam to a first collimator mirror for developing, from the diverging beam, a collimated beam, directing the collimated beam towards a diffraction grating, the grating dispersing the collimated beam according to wavelength into multiple beams, directing the beams to a second collimator mirror and reflecting the multiple divergent beams into convergent beams directed at selected positions at a plane, and processing the intensity of the light beam at the plane at different wavelengths to determine absorbance as a measure of concentration.

24. A method as claimed in claim 23 including operationally connecting a detector photoarray at the plane thereby to obtain the intensity signal of selected wavelengths of the beam, and processing the intensity signals to obtain absorbance values at different wavelengths.

25. A method as claimed in claim 24 determining changes in the concentration.

26. A system of determining the concentration of at least one chromophore substance in a sample comprising:
   (a) a lamp for generating a flashing light beam to pass through the sample containing the chromophore substance;
   (b) means for measuring the absorbance values by the sample at different wavelengths; and
   (c) means for determining the absorbance values at the different wavelengths thereby to obtain a measure of the chromophore concentration.

27. A system as claimed in claim 26 wherein errors in absorbance values are mutually correlated at different wavelengths, and including means for determining a linear combination of the absorbance values to reflect this correlation.

28. A system as claimed in claim 27 wherein the linear combination reflects the nature of correlated errors and the direction of extinction coefficients of a chromophore in the sample, and including means for measuring changes in the chromophore concentration.

29. A system as claimed in claim 28 including means for measuring the absorbance values for about five different wavelengths.

30. A method as claimed in claim 1 wherein the optimum linear combination is determined.

31. A method as claimed in claim 21 wherein the optimum linear combination is determined.

32. A system of claim 26 including the means for determining the optimum linear combination.

33. A method as claimed in claim 30 wherein the optimum linear combination is determined according to the constraints of $k \times e = 1$ and $k \times F \times k'$ being a minimum, where k reflects a row matrix consisting of the coefficients of the linear combination, e is a column matrix of extinction coefficients of a chromophore, and F is a covariance error matrix., and the constituents of k are according to the formula $k = (3' \times F^{-1} \times e)^{-1} \times e' \times F^{-1}$, wherein e' is the matrix transpose of e and $F^{-1}$ is the matrix inverse of F.

34. A method as claimed in claim 30 wherein there are more than two wavelengths.

35. A monobeam system comprising a lamp for flashing a light beam through a sample, means for dispersing the light beam passing through the sample into multiple wavelengths, and means for obtaining the intensity of the signal of the light beam at selected multiple wavelengths, and including a monochromator for dispersing the light beam from a flash lamp, optics for directing the light beam from the flash lamp, the monochromator including a first collimator mirror for developing, from the diverging beam, a collimated beam directed towards a diffraction grating, the grating dispersing the collimated beam according to wavelength, and a second collimator mirror receiving the multiple beams and reflecting the multiple beams into convergent beams at selected positions at a plane, the plane being located at a predetermined position for different wavelengths of the convergent beams.

36. A system as claimed in claim 35 including order sorting filters located at about the plane.

37. A system as claimed in claim 36 including a toroid mirror for directing the light beam from the flash lamp through a sample holder towards a slit located in close adjacency with the lens such that a selected portion of the light beam passes through the slit and is directed to the first collimator mirror.

38. A system as claimed in claim 37, including a detector photoarray at the plane to receive a beam of at least ten different wavelengths, a slit array located ahead of the detector photoarray such that selected different wavelengths of the beam pass to the detector photoarray.

39. A system as claimed in claim 37 including an electronic module operationally connected with the detector photoarray thereby to receive in analog form the intensity signal of selected wavelengths of the beam, means for processing the analog intensity signals to obtain digital absorbance such data being related to the intensity signals, processor means for processing the digital data to obtain measurement of absorbance values at different wavelengths, and processor means for determining consequent concentration values from the absorbance values.

40. A system as claimed in claim 39 means for determining changes in the concentration.

41. Apparatus operationally connected with an output detector photoarray of a monochromator from a monobeam system, the photoarray being adapted to receive, in analog form, an intensity signal of selected wavelengths of the beam related to a sample in a path of the beam, and comprising means for processing the analog intensity signals to obtain digital absorbance signal data and including processor means for processing the digital data to obtain a linear combination of absorbance values at the different wavelengths, and means for determining consequent concentration values from the absorbance values.

42. Apparatus as claimed in claim 41 including means for determining concentration changes.

43. Apparatus as claimed in claim 41 wherein the analog intensity signals are at about ten wavelengths and including multiplexer means for receiving the signals, means for outputting about five wavelength intensity signals, and means for converting said five wavelength intensity signals to a log digital signal representative of absorbance values at the five wavelengths.

44. Apparatus as claimed in claim 43 including means for multiplexing absorbance value analog signals into absorbance digital signals to provide an output for the processing means.

45. Apparatus as claimed in claim 44 wherein the processor means operates the linear combination according to constraints of $k \times e = 1$ and the noise being represented by $k \times F \times k'$ as a mean square error being a minimum where k is a row matrix consisting of the coefficients of the linear combination, F is covariance error matrix of f, and k' is the matrix transpose of k, e is a column matrix of extinction coefficients of the chromophores, and f is a column matrix representing errors.

46. Apparatus as claimed in claim 45 wherein the linear combination is the optimum linear combination.

47. A method of measuring the concentration of at least one chromophore substance in a sample comprising:
    (a) flashing a lamp to generate a flashing light beam to pass through the sample containing the chromophore substance;
    (b) measuring absorbance values by the sample at different wavelengths; and
    (c) determining an optimum of the absorbance values at the different wavelengths thereby to obtain a measure of the chromophore concentration.

48. A method of determining an optimum of absorbance values at different wavelengths of a light beam passing through a sample chromophore substance in a sample comprising:
    (a) flashing a lamp to generate a flashing light beam to pass through the sample containing the chromophore substance; and
    (b) measuring the absorbance values by the sample at different wavelengths, wherein errors in absorbance values are at different optimum wavelengths.

* * * * *